US012655256B2

(12) United States Patent
Khademhosseini et al.

(10) Patent No.: US 12,655,256 B2
(45) Date of Patent: Jun. 16, 2026

(54) MICRO-ENGINEERED POLY(HEMA) HYDROGEL FOR WEARABLE CONTACT LENS BIOSENSING AND OTHER APPLICATIONS

(71) Applicants: THE REGENTS OF THE UNIVERSITY OF CALIFORNIA, Oakland, CA (US); COOPERVISION INTERNATIONAL LIMITED, Fareham (GB)

(72) Inventors: Alireza Khademhosseini, Los Angeles, CA (US); Shiming Zhang, Hong Kong (CN); Sourav Saha, Pleasanton, CA (US); Mehmet R. Dokmeci, Los Angeles, CA (US); Lu Jiang, Pleasanton, CA (US)

(73) Assignees: THE REGENTS OF THE UNIVERSITY OF CALIFORNIA, Oakland, CA (US); COOPERVISION INTERNATIONAL LIMITED, Fareham. (GB)

( * ) Notice: Subject to any disclaimer, the term of this patent is extended or adjusted under 35 U.S.C. 154(b) by 654 days.

(21) Appl. No.: 18/042,598

(22) PCT Filed: Sep. 16, 2021

(86) PCT No.: PCT/US2021/050735
§ 371 (c)(1),
(2) Date: Feb. 23, 2023

(87) PCT Pub. No.: WO2022/061028
PCT Pub. Date: Mar. 24, 2022

(65) Prior Publication Data
US 2023/0331935 A1       Oct. 19, 2023

Related U.S. Application Data

(60) Provisional application No. 63/080,425, filed on Sep. 18, 2020.

(51) Int. Cl.
| | | |
|---|---|---|
| *A61B 5/145* | (2006.01) | |
| *A61B 5/1477* | (2006.01) | |
| (Continued) | | |

(52) U.S. Cl.
CPC ........... *C08J 3/075* (2013.01); *A61B 5/14507* (2013.01); *A61B 5/14546* (2013.01);
(Continued)

(58) Field of Classification Search
CPC .......... A61B 2562/028; A61B 2562/12; A61B 5/6821; A61B 5/14507; A61B 5/14546;
(Continued)

(56) References Cited

U.S. PATENT DOCUMENTS

| | | | | | |
|---|---|---|---|---|---|
| 5,453,467 | A | * | 9/1995 | Bamford | ................. C08L 75/16 |
| | | | | | 525/422 |
| 6,217,171 | B1 | * | 4/2001 | Auten | ...................... G02C 7/12 |
| | | | | | 351/159.02 |

(Continued)

FOREIGN PATENT DOCUMENTS

| | | |
|---|---|---|
| CN | 109 288 619 A | 2/2019 |
| WO | WO 2021/005326 | 1/2021 |

(Continued)

OTHER PUBLICATIONS

Yetisen, Ali K., et al. "Scleral lens sensor for ocular electrolyte analysis." Advanced materials 32.6 (2020): 1906762. (Year: 2019).*

(Continued)

*Primary Examiner* — Eric J Messersmith
(74) *Attorney, Agent, or Firm* — VISTA IP LAW GROUP LLP

(57) ABSTRACT

Microchannels in hydrogels play an essential role in enabling a smart contact lens. A wearable contact lens is disclosed herein that uses microchannels and connected chambers located in poly-2-hydroxyethyl methacrylate (Continued)

(poly(HEMA)) hydrogel that is used in a commercial contact lens with three-dimensional (3D) printed mold. The corresponding capillary flow behaviors in these microchannels were investigated. Different capillary flow regimes were observed in these microchannels, depending on the hydration level of the hydrogel material. In particular, it was found that a peristaltic pressure could reinstate flow in a dehydrated microchannel, indicating the motion of eye-blinking may help tear flow in a microchannel-containing contact lens. Colorimetric pH and electrochemical $Na^+$ sensing capabilities were demonstrated in these microchannels. Micro-engineered contact lenses formed using poly (HEMA) hydrogel can be used for various biomedical applications such as eye-care and wearable biosensing.

16 Claims, 10 Drawing Sheets

(51) Int. Cl.

| | |
|---|---|
| *A61F 9/00* | (2006.01) |
| *B29D 11/00* | (2006.01) |
| *C08J 3/075* | (2006.01) |
| *G02B 1/04* | (2006.01) |
| *G02C 7/04* | (2006.01) |
| *B29K 33/00* | (2006.01) |
| *B29K 105/00* | (2006.01) |

(52) U.S. Cl.
CPC .......... *A61B 5/1477* (2013.01); *A61F 9/0017* (2013.01); *B29D 11/00048* (2013.01); *B29D 11/00096* (2013.01); *G02B 1/043* (2013.01); *G02C 7/049* (2013.01); *B29K 2033/12* (2013.01); *B29K 2105/0061* (2013.01); *C08J 2333/10* (2013.01); *C08J 2481/08* (2013.01)

(58) Field of Classification Search
CPC ..... A61B 5/1477; C08J 3/075; C08J 2333/10; C08J 2481/08; A61F 9/0017; B29D 11/00048; B29D 11/00096; G02B 1/043; G02C 7/049; B29K 2033/12; B29K 2105/0061
See application file for complete search history.

(56) References Cited

U.S. PATENT DOCUMENTS

| | | | | |
|---|---|---|---|---|
| 9,688,741 | B2 | 6/2017 | Annabi et al. | |
| 9,789,655 | B1* | 10/2017 | Weibel | B29C 37/0067 |
| 10,085,637 | B2* | 10/2018 | Araci | B29D 11/0073 |
| 11,550,166 | B2 | 1/2023 | Saha et al. | |
| 2006/0154894 | A1 | 7/2006 | Berry et al. | |
| 2006/0290882 | A1* | 12/2006 | Meyers | G02C 7/049 |
| | | | | 351/159.62 |
| 2008/0102276 | A1 | 5/2008 | Khademhosseini et al. | |
| 2013/0090612 | A1 | 4/2013 | de Juan, Jr. et al. | |
| 2014/0088381 | A1 | 3/2014 | Etzkorn et al. | |
| 2015/0173658 | A1 | 6/2015 | Liu et al. | |
| 2015/0201837 | A1 | 7/2015 | Song et al. | |
| 2018/0299699 | A1* | 10/2018 | Wei | G02C 7/049 |
| 2019/0048180 | A1 | 2/2019 | Harant et al. | |
| 2019/0076021 | A1* | 3/2019 | Araci | G02C 7/04 |
| 2019/0086693 | A1 | 3/2019 | Blum et al. | |
| 2020/0116664 | A1* | 4/2020 | Abeyrathne | G01N 27/301 |
| 2020/0122140 | A1 | 4/2020 | Zhang et al. | |
| 2020/0214887 | A1 | 7/2020 | Gutierrez | |
| 2020/0257138 | A1 | 8/2020 | Iwasaki | |
| 2020/0324469 | A1 | 10/2020 | Zhang et al. | |
| 2020/0377677 | A1* | 12/2020 | Zhao | C08L 101/12 |

| | | | | |
|---|---|---|---|---|
| 2021/0124186 | A1* | 4/2021 | Oag | G02C 11/10 |
| 2021/0353829 | A1 | 11/2021 | Khademhosseini et al. | |
| 2022/0413321 | A1* | 12/2022 | Oag | G02C 11/10 |

FOREIGN PATENT DOCUMENTS

| | | |
|---|---|---|
| WO | WO 2022/043681 | 3/2022 |
| WO | WO-2022/061028 | 3/2022 |

OTHER PUBLICATIONS

Yang, Xing, et al. "Flexible, wearable microfluidic contact lens with capillary networks for tear diagnostics." Journal of Materials Science 55.22 (2020): 9551-9561. (Year: 2020).*
Wei, Shiyuan, et al. "Gas-permeable, irritation-free, transparent hydrogel contact lens devices with metal-coated nanofiber mesh for eye interfacing." ACS nano 13.7 (2019): 7920-7929. (Year: 2019).*
Yao, H., et al. "A soft hydrogel contact lens with an encapsulated sensor for tear glucose monitoring." 2012 IEEE 25th International Conference on Micro Electro Mechanical Systems (MEMS). IEEE, 2012. (Year: 2012).*
Jiang, Nan, et al. "Microfluidic contact lenses." Small 14.15 (2018): 1704363. (Year: 2018).*
Yetisen, Ali K., et al. "Capillary flow in microchannel circuitry of scleral lenses." RSC advances 9.20 (2019): 11186-11193. (Year: 2019).*
Moreddu, Rosalia, et al. "Integration of paper microfluidic sensors into contact lenses for tear fluid analysis." Lab on a Chip 20.21 (2020): 3970-3979. (Year: 2020).*
PCT International Search Report for PCT/US2021/050735, Applicant: The Regents of the University of California, Form PCT/ISA/210 and 220, dated Feb. 3, 2022 (5 pages).
PCT Written Opinion of the International Search Authority for PCT/US2021/050735, Applicant: The Regents of the University of California, Form PCT/ISA/237, dated Feb. 3, 2022 (6 pages).
Alex J Cadotte et al., Poly-HEMA as a drug delivery device for in vitro neural networks on micro-electrode arrays, J. Neural Eng. 2 (2005) 114-122.
Yu-Chih Chen et al., High-Throughput Single-Cell Derived Sphere Formation for Cancer Stem-Like Cell Identification and Analysis, Scientific Reports, 6:27301, DOI:10.1038/srep27301.
Seung Woo Choi et al., Therapeutic Contact Lenses with Polymeric Vehicles for Ocular Drug Delivery: A Review, Materials (2018), 11, 1125; doi:10.3390/ma11071125.
Muhammad Imran et al., Fabrication of microchannels on PMMA using a low power CO2 laser, Laser Phys. 26 (2016) 096101 (7 pages).
Rosalia Moreddu et al., Contact Lens Technology: From Fundamentals to Applications, Advanced Healthcare Materials, vol. 8, No. 15, 1900368. https://doi.org/10.1002/adhm.201900368.
Christopher Stephen Andrew Musgrave et al., Contact Lens Materials: A Materials Science Perspective, Materials Dec. 2019, 261; doi: 10.3390/ma12020261 (35 pages).
Ryan Chang Tseng et al., Contact-Lens Biosensors, Sensors 2018, 18, 2651; doi: 10.3390/s18082651 (24 pages).
Yiran Yang et al., Wearable and flexible electronics for continuous molecular monitoring, Chem. Soc. Rev., 2019, 48, 1465-1491.
PCT International Preliminary Report on Patentability (Chapter I of the Patent Cooperation Treaty) for PCT/US2021/050735, Applicant: The Regents of the University of California, Form PCT/IB/326 and 373, dated Mar. 30, 2023 (8 pages).
The extended European search report dated Feb. 15, 2024 for European Patent Application No. 21870242.1, Applicant: The Regents of University of California (8 pages).
H. Yao et al., A Soft Hydrogel Contact Lens with an Encapsulated Sensor for Tear Glucose Monitoring, Micro Electro Mechanical Systems (MEMS), 2012, IEEE 25th International Conference, IEEE, Jan. 29, 2012, pp. 769-772, XP032137360.
Response to the extended European search report dated Sep. 3, 2024

(56) References Cited

OTHER PUBLICATIONS for European Patent Application No. 21870242.1, Applicant: The
Regents of University of California (12 pages).

* cited by examiner

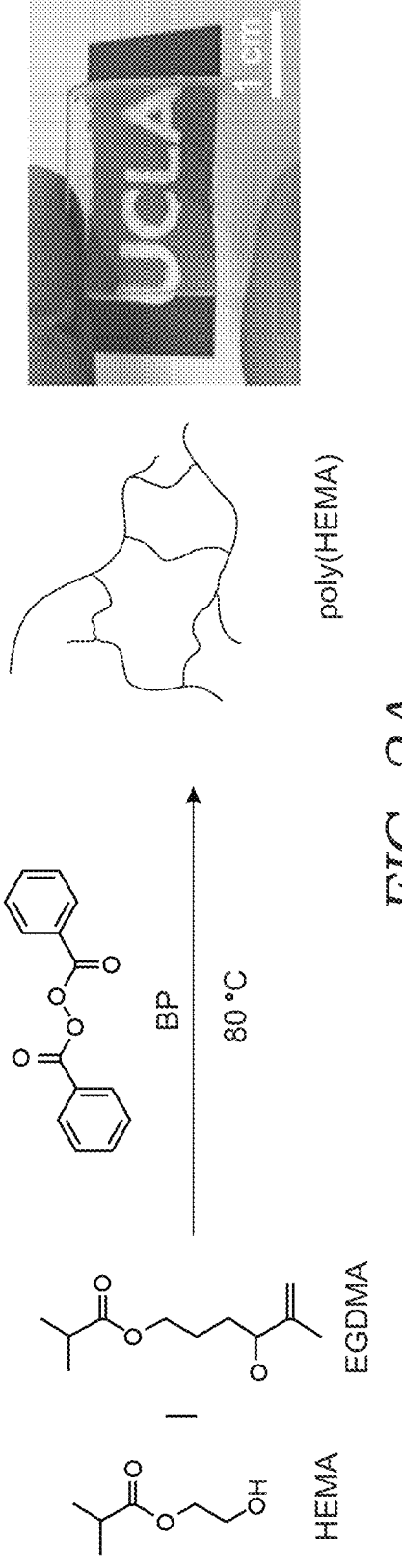
FIG. 2A
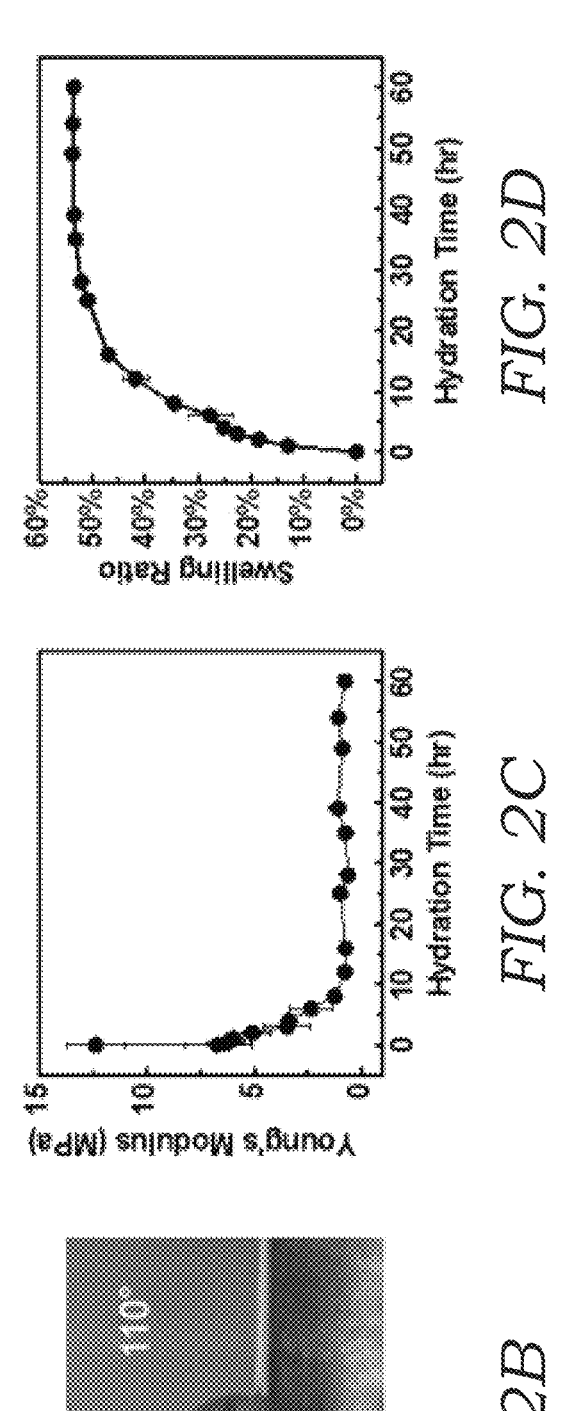
FIG. 2C
FIG. 2D
FIG. 2B

54

54

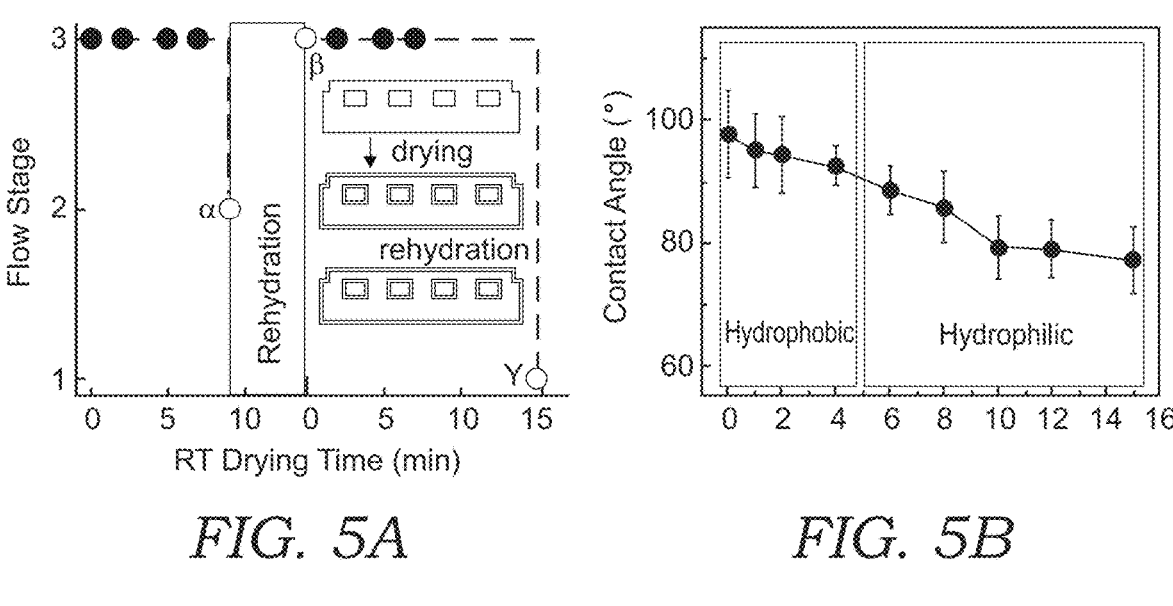
FIG. 5A          FIG. 5B
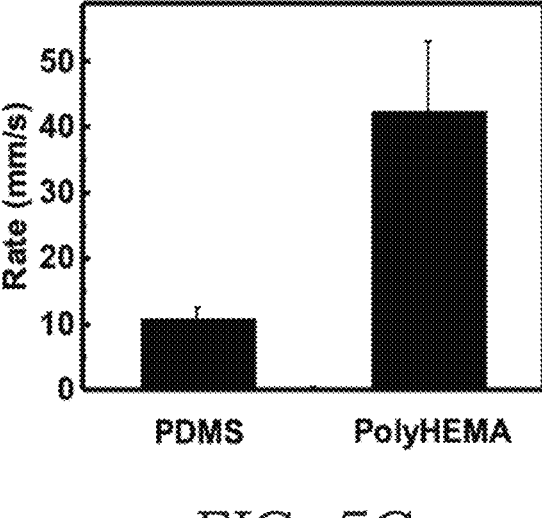
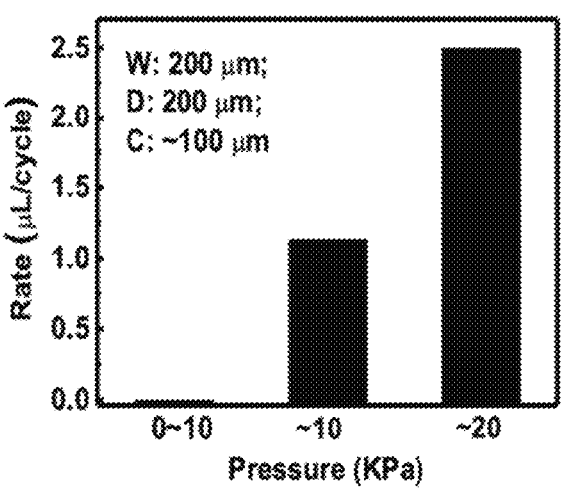
FIG. 5C          FIG. 5D

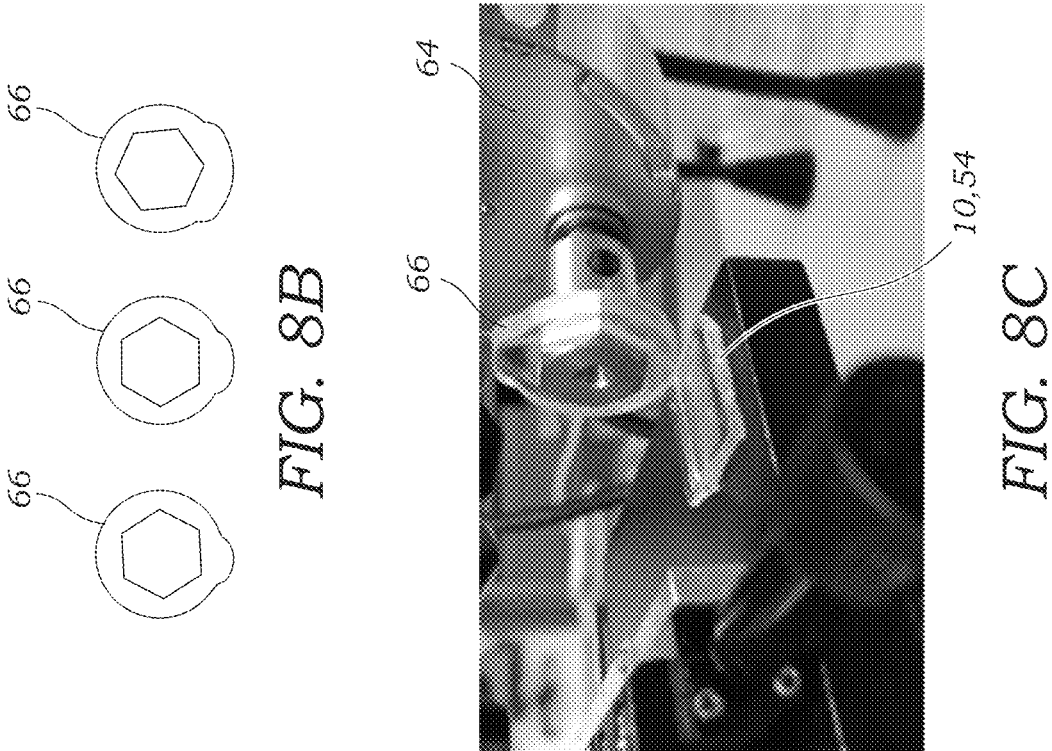
*FIG. 8B*
*FIG. 8C*
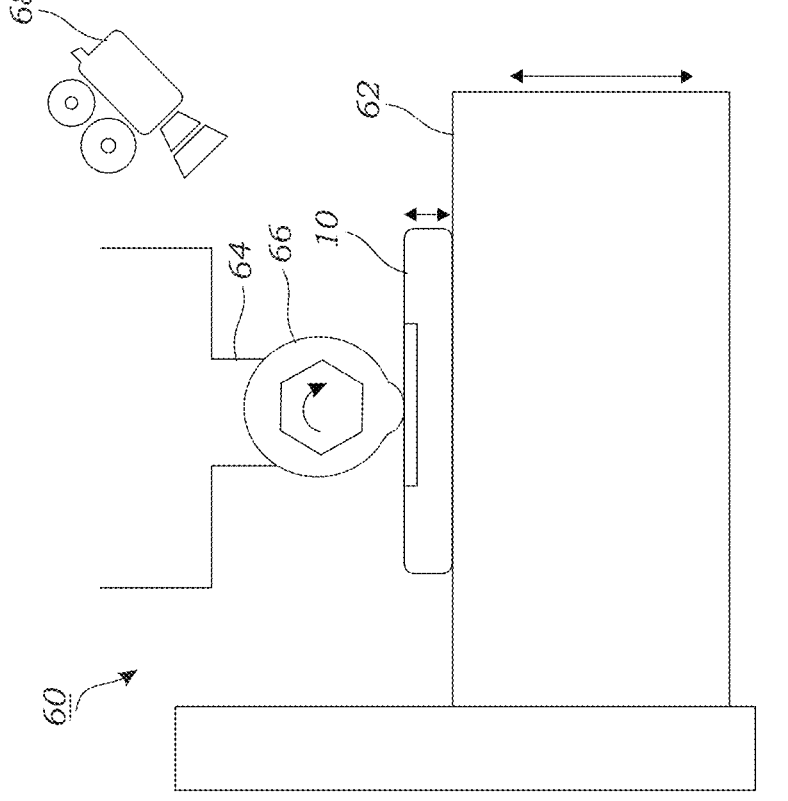
*FIG. 8A*

MICRO-ENGINEERED POLY(HEMA) HYDROGEL FOR WEARABLE CONTACT LENS BIOSENSING AND OTHER APPLICATIONS

RELATED APPLICATION

This Application is a U.S. National Stage filing under 35 U.S.C. § 371 of International Application No. PCT/US2021/050735, filed on Sep. 16, 2021, which claims priority to U.S. Provisional Patent Application No. 63/080,425 filed on Sep. 18, 2020, which are hereby incorporated by reference. Priority is claimed pursuant to 35 U.S.C. §§ 119, 371 and any other applicable statute.

TECHNICAL FIELD

The technical field relates to wearable contact lenses. More specifically, the technical field relates to wearable contact lenses for biosensing and other applications. The wearable contact lenses may be used to sense various analytes and physiological conditions using tears.

BACKGROUND

Noninvasive wearable biosensors, that can be used to detect biomarkers in bodily fluids such as sweat, saliva, and tear may one day replace some of these conventional medical instruments for various diagnostic applications. Compared to sweat- and saliva-sensing, tear-sensing is a more competitive technology because the concentration of biomarkers in tear is reported to be more related to that in blood. Besides, the tear is less likely to be contaminated, and its sensing is less susceptible to other factors such as secretion rate, evaporation, and temperature. Therefore, adding biosensing functions to commercial contact lenses, one of the most accepted wearable devices by the public, holds enormous commercial potential. For example, real-time monitoring of electrolyte concentration in tear, such as sodium ion ($Na^+$), could predict the occurrence of dry-eye. Measuring pH changes in tear could reflect drug effectiveness and other clinical signs in disease processes, while the continuous monitoring of glucose concentration could help early diagnosis of diabetes.

To avoid potential adverse effect on wearing comfortability and to protect the sensing elements from delamination and contamination, contact lenses need to be micromachined to have encapsulated microchannels and microchambers. These encapsulated channels and chambers are ideal places where the biosensors will be integrated.

Further enabling a guided tear flow in these microchannels is essential to collect and to distribute tear fluid to specific sensing areas. As of now, several methods have been proposed for prototyping microchannels in contact lenses; however, they were mostly demonstrated with non-commercial materials such as silicone elastomers that are easy to be micromachined. Although poly(HEMA) hydrogel has excellent biocompatibility, softness, and transparency, it is not compatible with mainstream microfabrication technologies. For example, soft lithography is compatible with polydimethylsiloxane (PDMS), but it is not readily adaptable for molding highly viscoelastic hydrogels. Photolithography can be used to microfabricate tiny structures in elastomers, whereas it is challenging to be used for hydrogels, which are susceptible to vacuum-, solvent-, and temperature-induced deformations. Dissolving and drying hydrogel powders in micro-molds is preferred when fabricating patterned thin hydrogel membranes, yet it remains challenging to obtain complex 3D structures. Laser ablation is another alternative, but it results in rough channel surfaces and non-uniform channel cross-sections.

SUMMARY

In one embodiment, a wearable contact lens formed from poly(HEMA) hydrogel is disclosed. The wearable contact lens may include one or more microchannels along with connected chambers formed therein that is/are used to transport fluid (e.g., tear fluid). The chambers may act as reservoirs for holding larger volumes of fluids and, in some embodiments, may contain reagents, drugs or therapeutic agents, or other fluids therein in one embodiment. The chambers may also be used hold fluid for various tasks such as holding or receiving a sample, storing of fluid, or testing of fluid. The chambers (or microchannels) may also include one or more sensors therein such as, for example, an electrochemical sensing electrode (e.g., $Na^+$ sensing electrode). In other embodiments, the sensor may include a colorimetric sensor.

In another embodiment, a method of making a wearable contact lens formed from poly(HEMA) hydrogel and having one or more microchannels formed therein is disclosed. In the method, micromachining of microchannels in poly(HEMA) hydrogel is used. An additive or 3D printing technique is used to create reverse molds for the microchannels. A systematic experimental effort was dedicated to identifying an optimized process flow that allows the molding and delaminating of the hydrogel from the 3D printed molds while maintaining smooth and well-defined microchannels after separation. Encapsulation of these microchannels with a capping layer was realized by either: (1) treating hydrogel surfaces with plasma or (2) using a non-crosslinked precursor as an adhesive layer. A qualitative study was performed to investigate the relationship between the flow behavior in these microchannels and the hydrogel hydration level. Significantly, it was revealed that an external peristaltic pressure could reinstate flow in the dehydrated microchannels. This phenomenon indicates that the motion of eye-blinking (which can apply external peristaltic pressure) can improve tear flow in a microchannel-containing contact lens. As an example of biosensing contact lens, colorimetric pH and electrochemical $Na^+$ biosensors were integrated into poly(HEMA) hydrogel microchannels (or chambers), which is relevant to tear osmolarity monitoring and dry-eye disease prevention. These findings promote the use of commercial poly(HEMA) hydrogel for various biomedical applications such as eye-care and wearable biosensing.

In another embodiment, a contact lens includes a lens body comprising poly-2-hydroxyethyl methacrylate (poly(HEMA)) hydrogel, the lens body having formed therein one or more microchannels, the one or more microchannels connected to a plurality of chambers. An inlet is fluidically coupled to one of the plurality of chambers and an outlet is fluidically coupled to one of the plurality of chambers. Fluid may enter the lens body via the inlet while the outlet permits fluid flow through the microchannels without trapping of air or gases. In some embodiments, fluid may also leave the contact lens via the outlet.

In another embodiment, a method of forming a contact lens with one or more microchannels formed therein including providing a mold having reverse features of the one or more microchannels and the plurality of chambers. Poly-2-hydroxyethyl methacrylate (poly(HEMA)) precursor mixture is then cast on the mold, the precursor mixture including HEMA, a free-radical initiator, and a crosslinking agent to form a poly(HEMA) layer. After crosslinking the poly (HEMA) layer is removed from the mold. A capping layer is then secured to the poly(HEMA) layer.

The contact lens (or a pair of lenses) may be worn by the user. The lens(es) can be used to sense and/or analyze physiological conditions of the user through tear fluid. Sensor(s) may be incorporated into the lens(es). In addition, the contact lens may include therapeutic agents or drugs therein that are released upon eye blinking movement of the wearer.

BRIEF DESCRIPTION OF THE DRAWINGS

FIG. 2A illustrates the synthesis of poly(HEMA) hydrogel (insert shows the transparent poly(HEMA) hydrogel).

FIG. 2B illustrates the contact angle measurement of an as-synthesized poly(HEMA) hydrogel.

FIG. 2C illustrates a graph of the Young's modulus as a function of increasing poly(HEMA) hydration levels.

FIG. 2D illustrates a graph of swelling ratio change as a function of increasing poly(HEMA) hydration levels.

FIGS. 4A-4D illustrates the flow volume collected in the drain chamber (i.e., reservoir) with time, and FIGS. 4E-4H) illustrates the corresponding flow behavior. In FIGS. 4A, 4E no flow was observed in a fully dehydrated poly(HEMA) microchannel (dried with nitrogen gun). FIGS. 4B, 4F illustrate peristaltic pressure (mimicking eye blinking) induced flow in mild hydrated poly(HEMA) microchannels. FIGS. 4C and 4G illustrates the transition from peristaltic pressure-induced flow to spontaneous capillary flow was observable after one more cycles of pressure. FIGS. 4D, 4H show the spontaneous flow observed directly in fully hydrated poly(HEMA) microchannels.

FIG. 5A shows a graph showing flow transition time from spontaneous capillary flow to pressure-activated flow and no flow by dehydrating a fully hydrated hydrogel in ambient conditions. The shadowed area indicates that the transition from stage 2 to stage 3 (5 min rehydration, started at the point $\beta$) by re-hydrating the sample. The inset illustrates the dehydration and rehydration processes in the poly(HEMA) microchannels.

FIG. 5B illustrates the contact angle change on a flat poly(HEMA) hydrogel surface during with increased hydration time (N=10, the measurements were performed in triplicates). The hydrogel was initially dehydrated with nitrogen gun (2 min).

FIG. 5C shows the comparison of flow rate in PDMS microchannels and poly(HEMA) microchannels (with microchannel width and depth of 200 $\mu$m). The flow rate in fully hydrated poly(HEMA) microchannels (~ 40 mm/s) was about four times faster than that in PDMS microchannels.

FIG. 5D illustrates that increasing the peristaltic pressure increased the volume of fluid delivered per pressure cycle (W/T/L of 200 $\mu$m/200 $\mu$m/16 mm). These results demonstrate that eye blinking may help flow exchange in the poly(HEMA) microchannels. The volumetric flow rate was estimated by measuring the increased volume of the fluid in the drain chamber after each pressure cycle. The rate represents the average value of multiple pressure cycles.

FIG. 6A shows the flow administration in microchannel-containing poly(HEMA) contact lens.

FIGS. 8A is a schematic representation of the flow visualization system used with experiments conducted herein.

FIG. 8B illustrates laser-ablated PMMA with different head shapes for peristaltic pressure application onto poly (HEMA) capping layer.

FIG. 8C illustrates a photographic image of the laser-ablated head applying pressure to poly(HEMA) hydrogel surface.

DETAILED DESCRIPTION OF ILLUSTRATED EMBODIMENTS

Figure 1A:
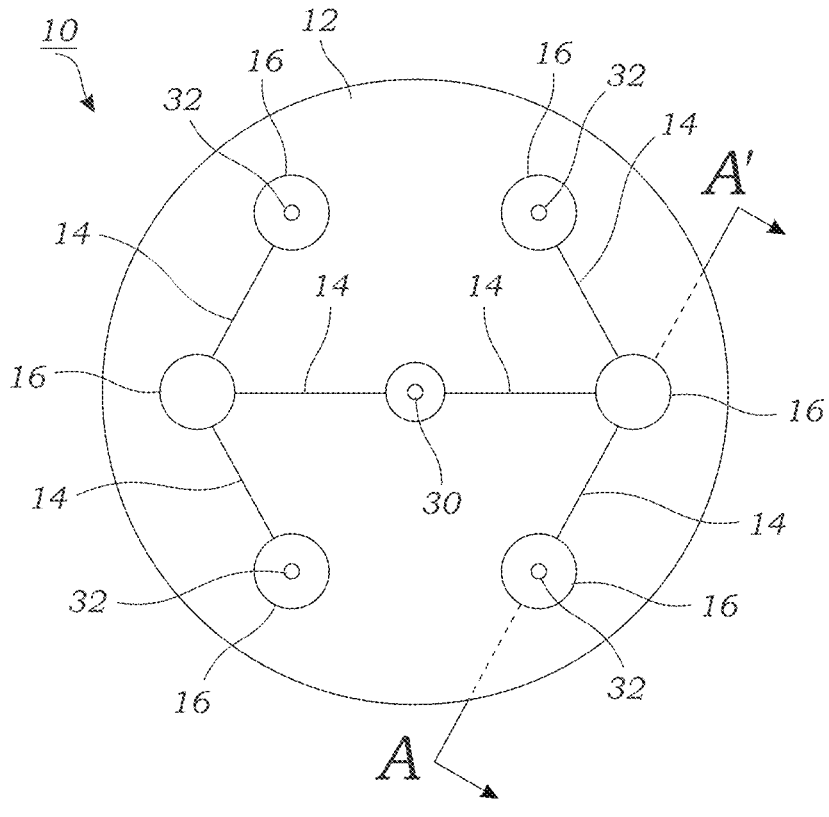
FIG. 1A illustrates one embodiment of a wearable contact lens having a plurality of chambers connected with a plurality of microchannels.
Figure 1B:
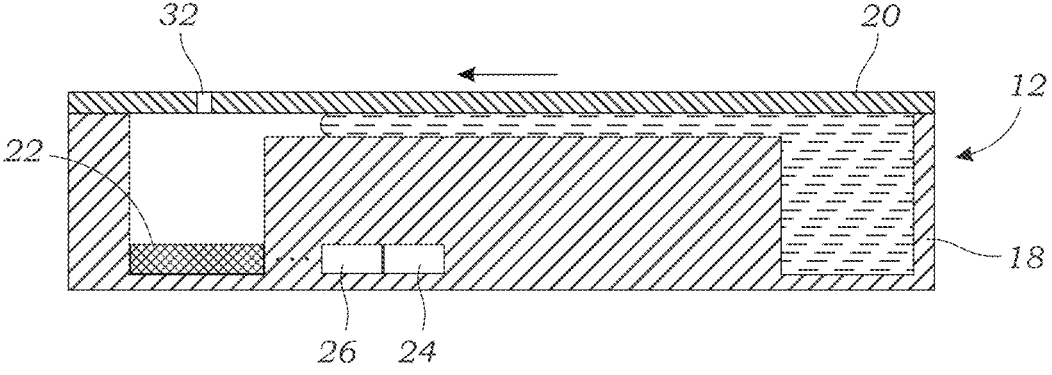
FIG. 1B illustrates a cross-sectional view of the contact lens of FIG. 1A taken along the line A-A'.

FIGS. 1A, 1B, 6B, 7A illustrate embodiments of a wearable contact lens 10. The wearable contact lens 10 includes a lens body 12 that includes one or more microchannels 14 formed therein that are used to transport fluids within the contact lens 10. The fluids that are transported may include tears or reagents. The microchannels 14 may have a width and depth that ranges from tens of micrometers to hundreds of micrometers. The length of the microchannels 14 may vary. The length may include tens of micrometers to hundreds of micrometers to tens of millimeters. The microchannels 14 are fluidically connected to chambers 16 which hold larger volumes of fluid. With reference to FIG. 1A, the microchannels 14 may be fluidically connected to a single chamber 16 or multiple chambers 16. The lens body 12 may be formed as a monolithic structure or as a laminate structure. FIG. 1B illustrates a laminate structure of the lens body 12 that includes a base layer 18 and a capping layer 20. The base layer 18 and the capping layer 20 are brought together and secured to one another via fabrication as explained herein.

The lens body 12 of the contact lens 10 is made from poly-2-hydroxyethyl methacrylate (poly(HEMA)). In some embodiments, both the base layer 18 and the capping layer 20 are made from poly(HEMA). In some embodiments, the wettability and/or oxygen permeability may be tuned by, for example, adding small quantities of negatively charged groups such as methacrylic acid (MA) or hydrophilic neutral groups such as polyvinyl alcohol (PVA) or N-vinyl pyrrolidone (NVP) to increase water content.

In some embodiments, the lens body 12 may include a sensor 22 that is used to sense, detect, and/or analyze the fluid that comes into contact with the sensor 22. In some embodiments, the sensor 22 may be a passive sensor that measures a property of tears. For example, the sensor 22 may include a colorimetric pH sensor that changes color in response to the pH of the contacting fluid. The color change may be monitored using, for example, an imaging device (e.g., camera or the like). In other embodiments, the sensor 22 may include an active sensor such as an electrochemical sensing electrode (e.g., $Na^+$ sensing electrode). For example, such a sensor 22 can be used to monitor tear osmolarity. The concentration of $Na^+$ is an essential health indicator in the tear that is relevant to tear osmolarity and dry-eye disease. The sensor 22 may also analyze or detect the presence of other tear species including, for example, proteins, enzymes, and peptides For active sensors 22, a power source 24 and control circuitry 26 may be embedded within the lens body 12 and used to power the active sensor 22 and acquire signals or data from the sensor 22. The sensor 22 may include the ability to transmit data remotely that can be interrogated by a reader device or the like so that contact lens 10 can transmit data wirelessly (e.g., using Bluetooth, WiFi, or near-filed communication). In some embodiments, the sensor 22 may be powered using a remote application of electromagnetic radiation or the like that powers the sensor 22 remotely.

The fluids that may be transported include tear fluid on the eye of the subject wearing the contact lens 10. The fluid enters the contact lens 10 via one or more inlets 30. The inlets 30 provide fluid communication from the external environment (i.e., surface of the eye) to the interior fluid passageways of the contact lens 10. For example, the one or more inlets 30 may be positioned over chambers 16 as illustrated in FIG. 1A. In addition, fluid may diffuse into the flow passages through the hydrogel matrix of the contact lens 10. In some embodiments, the contact lens 10 includes one or more outlets 32 that allow air or gas that is contained in the microchannels 14 or chambers 16 to exit the contact lens 10 as these fluid regions are filled with fluid. The one or more outlets 32 also allow, in some embodiments, fluid to exit the internal flow passages (i.e., microchannels 14 and/or chambers 16) and flow to the external environment (e.g., surface of the eye). For example, tear may return back to the eye. In another embodiment, one or more therapeutic agents are contained in the microchannels 14 and/or chambers 16 and are solubilized after contact with tear fluid and then delivered to the eye via the one or more outlets 32. The chambers 16 (or the one or more microchannels 14) may also contain reagents, reporter molecules, and other fluids therein. Alternatively, the therapeutic agent may diffuse out of the contact lens 10 rather than through one or more dedicated outlets 32.

Optional valves may be located in the one or more microchannels 14 and are used to modulate the flow of fluid into or from the microchannels 14. For example, valves may be used to modulate flow in only one direction. The fluid pathways inside the wearable contact lens 10 may also contain dry or lyophilized reagents, drug or therapeutic agent, or the like that are dissolved into fluid form once exposed to tear fluid of the eye. In still other embodiments, the fluid passageways may form generally closed passageways that allow for inflow or intrusion of tears while keeping reagents, products, and like that are generated inside the contact lens 10.

Figures 4A, 4B, 4C, 4D, 4E, 4F, 4G, 4H:
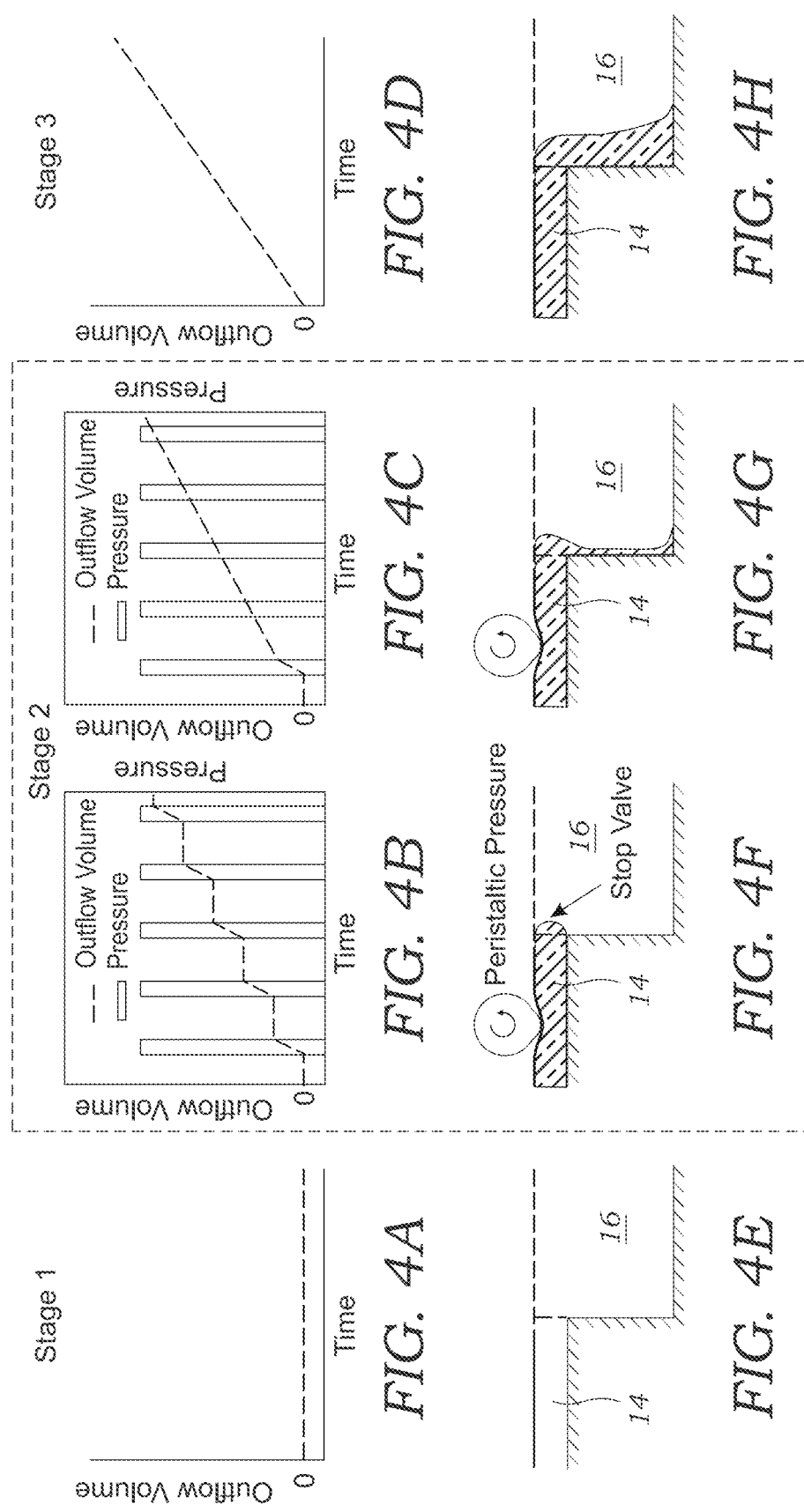
FIGS. 4A-4H illustrates the identified flow stages in poly(HEMA) microchannels, depending on the hydration level of the poly(HEMA).

The contact lens 10 is used by placing the same in the eye(s) of the mammalian subject as is done with conventional contact lenses. As explained herein, tear present on or within the eye can enter the fluid pathways of the contact lens 10 via the inlet(s) 30. This fluid may accumulate and fill, for example, the chamber(s) 16. In one embodiment, the act of eye blinking is used to move fluid through the microchannels 14. Eye blinking movement applies pressure to the contact lens 10 (e.g., the capping layer 20) resulting in peristaltic pressure-induced flow of fluid within the microchannel(s) 14. This flow may also transition to spontaneous flow within the microchannels 14 (e.g., FIGS. 4C and 4G). Eye blinking for example, can be used to rehydrate or increase the water contact of the contact lens 10 by flowing fluid through the microchannel(s) 14. Eye blinking can also be used to introduce fluid to solubilize therapeutic agents that may be stored or contained in the microchannels 14 or chambers 16.

Experimental

Results and Discussions

Poly(HEMA) hydrogel was synthesized by optimizing concentrations of the monomer, 2-hydroxyethyl methacrylate (HEMA), the cross-linker, ethylene glycol dimethacrylate (EGDMA), and the thermal initiator, benzoyl peroxide (BP) in the precursor solution, as illustrated in FIG. 2A. In this experiment, poly(HEMA) hydrogel 54 was formed having a plurality of microchannels 14 connected to chambers 16. The poly(HEMA) hydrogel 54 did not take the form of a lens body 12 but more approximated a microfluidic device. The as-synthesized poly(HEMA) hydrogel exhibited a high contact angle (about 110°, as shown in FIG. 2B). The Young's modulus of the as-synthesized poly(HEMA) hydrogel was about 12 MPa (FIG. 2C). However, after hydration in deionized water at room temperature, the Young's modulus of the poly(HEMA) hydrogel 54 quickly decreased to 1 MPa within eight (8) hours. The contact angle also reduced to ~60° due to increased water content. The poly(HEMA) hydrogel 54 had a swelling ratio of ~1.5 after 24 hours of immersion in water at room temperature (FIG. 2D).

Figure 3A:
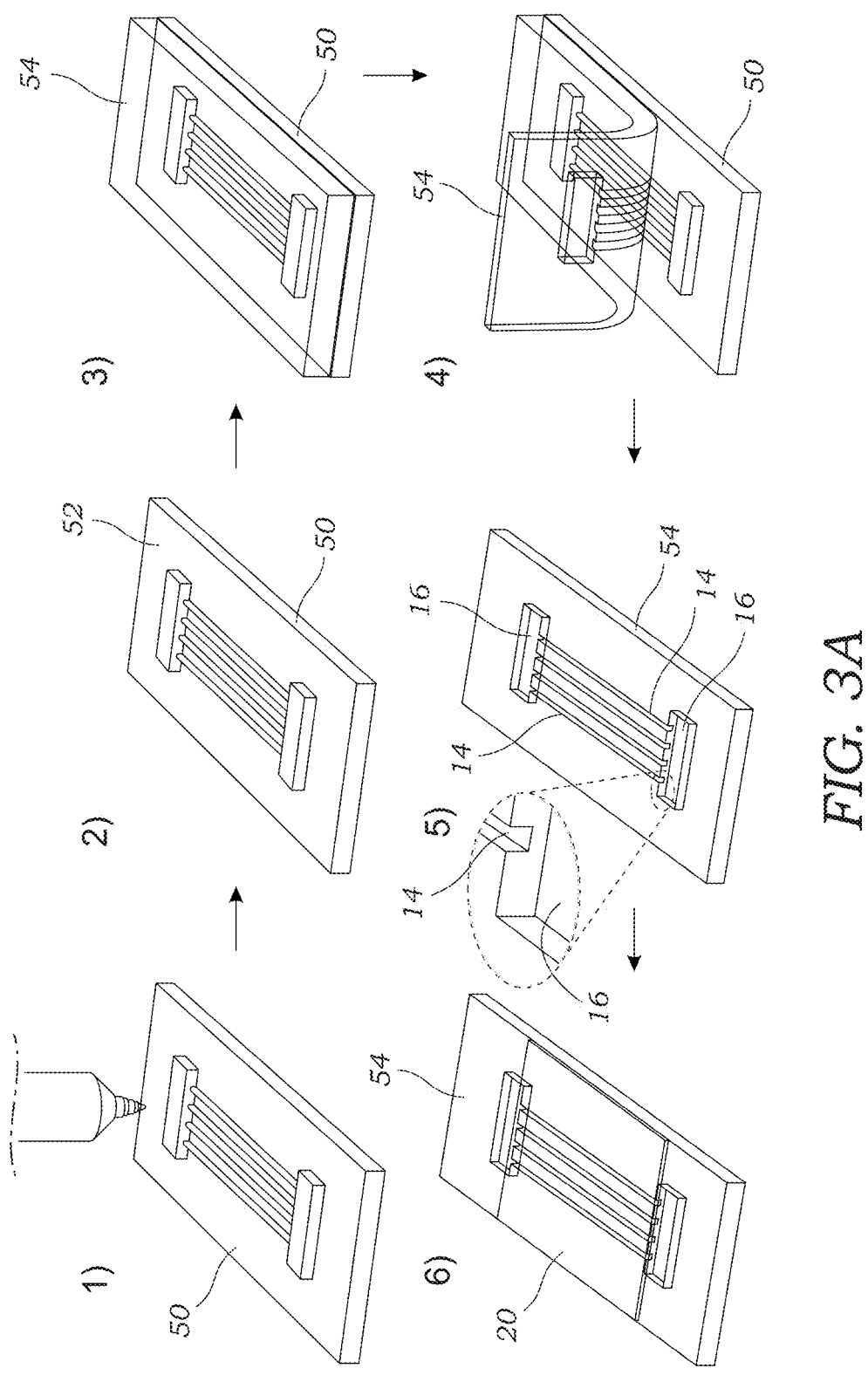
FIG. 3A illustrates a process flow of fabricating encapsulated microchannels in a poly(HEMA) hydrogel with a combination of 3D printing and replication. It includes: 1) 3D printing of a reverse mold; 2) deposition of 2-$\mu$m-thick Parylene layer on the mold to ease future delamination; 3) casting the poly(HEMA) precursor on the mold; 4) delamination of the poly(HEMA) hydrogel, 5) flattening the micromachined poly(HEMA) hydrogel, and 6) encapsulation of the poly(HEMA) microchannels with a thin poly(HEMA) capping layer.
Figure 3E:
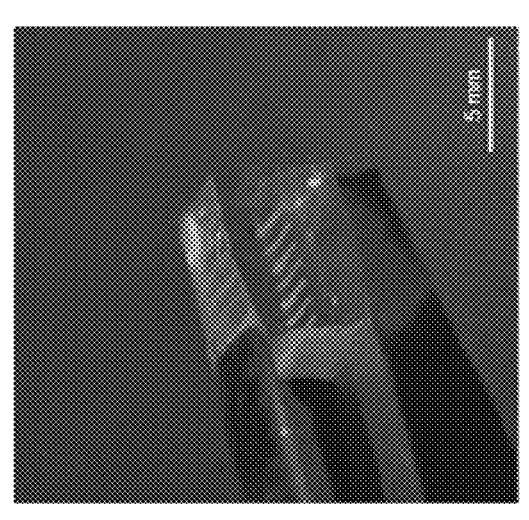
FIG. 3E shows the encapsulation of poly(HEMA) microchannels (bottom) with a poly(HEMA) capping layer (top) via plasma-assisted bonding.
Figure 3F:
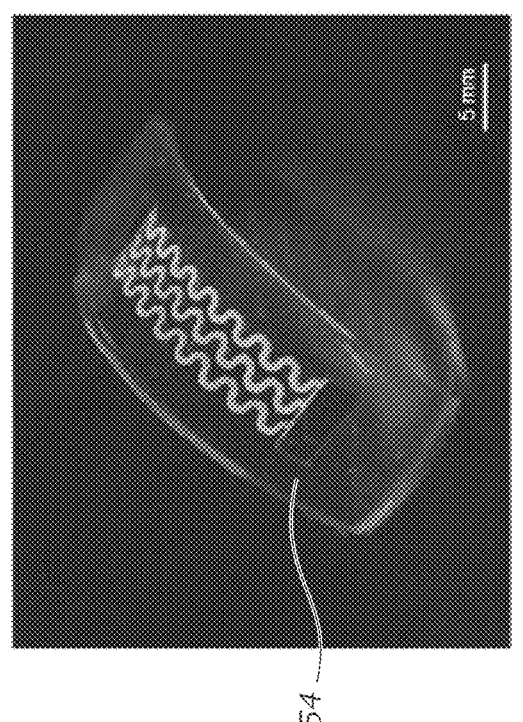
FIG. 3F illustrates poly(HEMA) hydrogel with serpentine-shaped poly(HEMA) microchannels with a microchannel width of 200 $\mu$m.
Figure 3F:
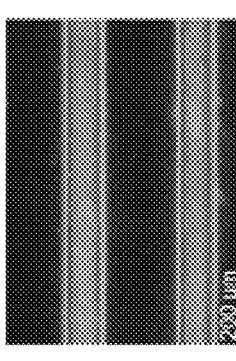
Figure 3B:
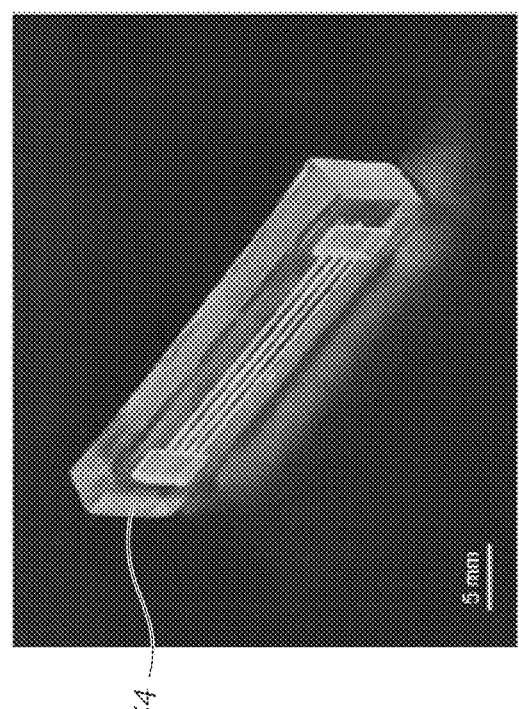
FIG. 3B illustrates an image of the poly(HEMA) hydrogel having encapsulated microchannels.
Figure 3C:
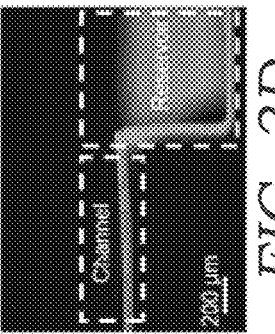
FIG. 3C illustrates an image of the straight poly(HEMA) microchannels with width and depth of 200 $\mu$m. The poly (HEMA) chambers have a depth of 500 $\mu$m.
Figure 3D:
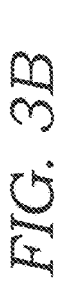
FIG. 3D shows a cross-section of poly(HEMA) microchannel (100 $\mu$m in width and depth) connecting to a chamber with a depth of 1 mm.
Figures 3G, 3H, 3I, 3J:
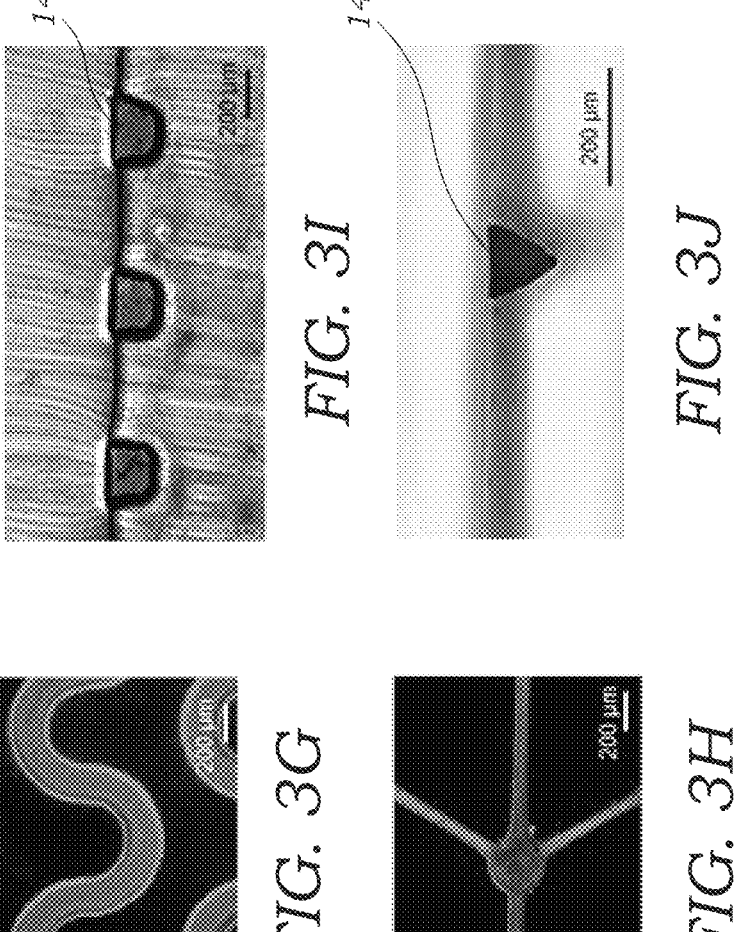
FIG. 3G illustrates an enlarged view of the serpentine-shaped poly(HEMA) microchannels of FIG. 3F.
FIG. 3H illustrates poly(HEMA) microchannels with a chamber connecting four branches in different directions.
FIG. 3I illustrates a cross-sectional image of encapsulated poly(HEMA) microchannels (200-$\mu$m in depth). The demonstrated microchannels were obtained from 3D printing and plasma-assisted bonding.
FIG. 3J illustrates a cross-sectional image of encapsulated poly(HEMA) microchannels (200-$\mu$m in depth). The demonstrated microchannels were obtained laser ablation and poly(HEMA)-precursor-assisted bonding.

The process flow of fabrication of microchannels 14 in poly(HEMA) hydrogel 54 is illustrated in FIG. 3A. High-resolution resin molds 50 were printed with a 3D printer (with a resolution of 30 μm). A 2-μm Parylene anti-adhesion layer 52 was deposited on the mold 50 to ease the future separation of hydrogel from the mold 50 after thermal crosslinking. Other polymer-based materials for the anti-adhesion layer 52. Next, poly(HEMA) precursor was cast onto the mold and polymerized to form poly(HEMA) hydrogel 54. After polymerization, the poly(HEMA) hydrogel 54 showed strong adhesion to the mold 50 and was not detachable. This critical issue was resolved by immersing the sample in hot water (80° C.) overnight. With this method, poly(HEMA) hydrogel 54 with smooth and well-defined microchannels 14 could be delaminated from the mold 50, with a thickness as thin as 1 mm. The delamination of the poly(HEMA) hydrogel 54 is illustrated in operation (4) of FIG. 3A.

To encapsulate microchannels 14 created in poly(HEMA) hydrogel 54, the following two methods were developed. In the first method, oxygen plasma was used to treat the surface of poly(HEMA) hydrogels to promote the bonding of microchannel-containing poly(HEMA) with a thin poly(HEMA) capping layer 20. Under the oxygen plasma atmosphere, the poly(HEMA) surface became hydrophilic due to the formation of radicals, alcohol, ester, carboxylic and carbonyl groups, by transposing the works describing the influence of plasma on poly(methyl methacrylate) (PMMA). Indeed, both polymers' pending groups display similar chemical structures. Bonding of two poly(HEMA) layers together was performed immediately after plasma treatment to avoid any reorganization of the polymer chain at the surface of the poly(HEMA). The newly formed low molecular weight chains, after the polymer chain scission by $O_2$/plasma, can migrate from the air-poly(HEMA) interface to the bulk of the material. The native polymer long chains move to the top surface by crawling, which generally leads to the initial surface energy recovery as shown for other polymers. Regarding the poly(HEMA) hydrogel 54 used herein, the crawling kinetic slowed down due to the reticulated structure.

In the second bonding method, the precursor of poly (HEMA) hydrogel was used as an adhesion promoter to crosslink two separated poly(HEMA) hydrogels 54 together. In this method, the poly(HEMA) precursor was spin-coated on the microchannel-containing poly(HEMA) hydrogel 54. Immediately after the spin-coating of the precursor solution onto the microchannel-containing hydrogel 54, the capping layer 20 was pressed atop, followed by a fully thermal crosslinking process in an oven. The second method is favorable towards a stronger bonding, whereas the first method is preferred when a dry encapsulation process is mandatory. If not emphasized, the plasma-assisted dry encapsulation method was used throughout the experiments described herein (FIGS. 3B-3J).

Visualization of flows in the microchannel-containing poly(HEMA) hydrogels 54 (FIGS. 3B, 3F) permits a qualitative study of flow dynamics using a flow visualization system 60 (FIG. 8A). The flow visualization system 60 includes a moveable stage 62 that holds a contact lens 10 and/or poly(HEMA) hydrogels 54. A rotary actuator 64 is mounted to various laser-ablated PMMA heads 66 (FIGS. 8B and 8C) to apply contact pressure to the contact lens 10 and/or poly(HEMA) hydrogels 54. Images are obtained using a recording camera 68 which, to ease visualization, a Smartphone camera was used. This practical setup is portable and permits an easy adjustment of the camera lens to the desired directions. In this design, a 10× macro lens was integrated with the camera 68 of the Smartphone, which enabled a close flow visualization in microchannels 14.

In short, three (3) flow stages were identified in the microchannel-containing poly(HEMA) hydrogel 54, which are dependent on the hydrogel's hydration level (qualitatively summarized in FIG. 4A-4D). In a dehydrated poly (HEMA) hydrogel 54, the surface was hydrophobic; therefore, no flow was observed (stage 1, FIG. 4A). In a fully hydrated poly(HEMA) hydrogel 54, a Laplace pressure-driven spontaneous capillary flow was observed (stage 3, FIG. 4D). Significantly, it was repeatedly observed that a transition stage existed between the fully hydrated and dehydrated stages, where the ceased flow was reinstated after the application of external peristaltic pressure (close to the pressure of eye-blinking) on the hydrogel capping layer 20 (stage 2, FIG. 4B). The observations of peristaltic pressure-induced flow in poly(HEMA) microchannels 14 represent one of the key findings. It indicates that eye-blinking pressure may help to promote tear flow within the microchannels 14 of the poly(HEMA) contact lens 10. It also supports the idea of eye-blinking assisted biosensing studies using contact lenses 10 to stimulate the development of smart contact lenses 10 for eye-care and wearable biosensing. Noteworthily, the peristaltic pressure-driven flow in stage 2 could transition to spontaneous flow after several pressure cycles (stage 2, and FIG. 4C), which was attributable to the increased hydration level of the hydrogel surface due to the inflow of the dye solution.

The reason that external peristaltic pressure was able to reinstate flow in stage 2 could be, at least partially, attributed to the abrupt geometric expansion at the junction between the microchannel 14 and the chamber 16 that acts as the drain reservoir ((FIGS. 3A, 3D and FIGS. 4E-4H)). It was surmised that when the flow meniscus reaches the microchannel 14/chamber 16 junction, the abrupt geometric change (in both microchannel width and depth) prevented the fluid meniscus to further advance. In this case, the application of an external peristaltic pressure repeatedly broke the established equilibrium state of the flow meniscus, which squeezed the liquid into the drain reservoir chamber 16 and helped to establish a new equilibrium state. The stage of peristaltic pressure-induced flow was maintained until the junction became sufficiently hydrated to induce a significant Laplace pressure that could reinstate a spontaneous flow (stage 3).

To evaluate the time required for the transition between the above-identified stages, time-varying flow visualization in these microchannels 14 was performed using the flow visualization system 60 illustrated in FIGS. 8A-8C. In this experiment, the surface of a fully hydrated hydrogel 54 was exposed to ambient air for different periods to dehydrate the sample. FIG. 5A shows the observed stages of the flow as a function of dehydration time. The results can be summarized as follows: i) spontaneous flow (stage 3) was maintained as long as the exposure time was less than 9 min; ii) spontaneous flow transited to pressure-induced flow (stage 2) when the exposure time was between 9 min and 15 min (started at the point α, showed in FIG. 5A); iii) the surface became hydrophobic, and no flow was observed (stage 1) when the exposure time was longer than 15 min (started at the point γ, showed in FIG. 5A). A contact angle of 100° was measured in a fully dehydrated and flat poly(HEMA) hydrogel surface, which decreased to 75° after water immersion for 15 min (FIG. 5B).

An accelerated flow rate in a microchannel 14 is preferred for advanced microfluidic applications. The flow rate in the micromachined poly(HEMA) hydrogel microchannels 14 is superior to that in a microchannel-containing elastomer. For example, the estimated flow rate in poly(HEMA) hydrogel 54 was about four times higher than that in PDMS-based microchannels with the same geometric profile (FIG. 5C). The volumetric flow rate per cycle was qualitatively evaluated as a function of applied pressure (stage 2, FIG. 5D). Upon applying a peristaltic pressure of ~10 kPa, a volumetric flow rate of ~1 μL/cycle was calculated, which increased to 2.5 μL/cycle when increasing the pressure to ~20 kPa. A quantitative study is encouraged to gain a deeper understanding of the dynamics.

Figures 6A, 6B, 6C:
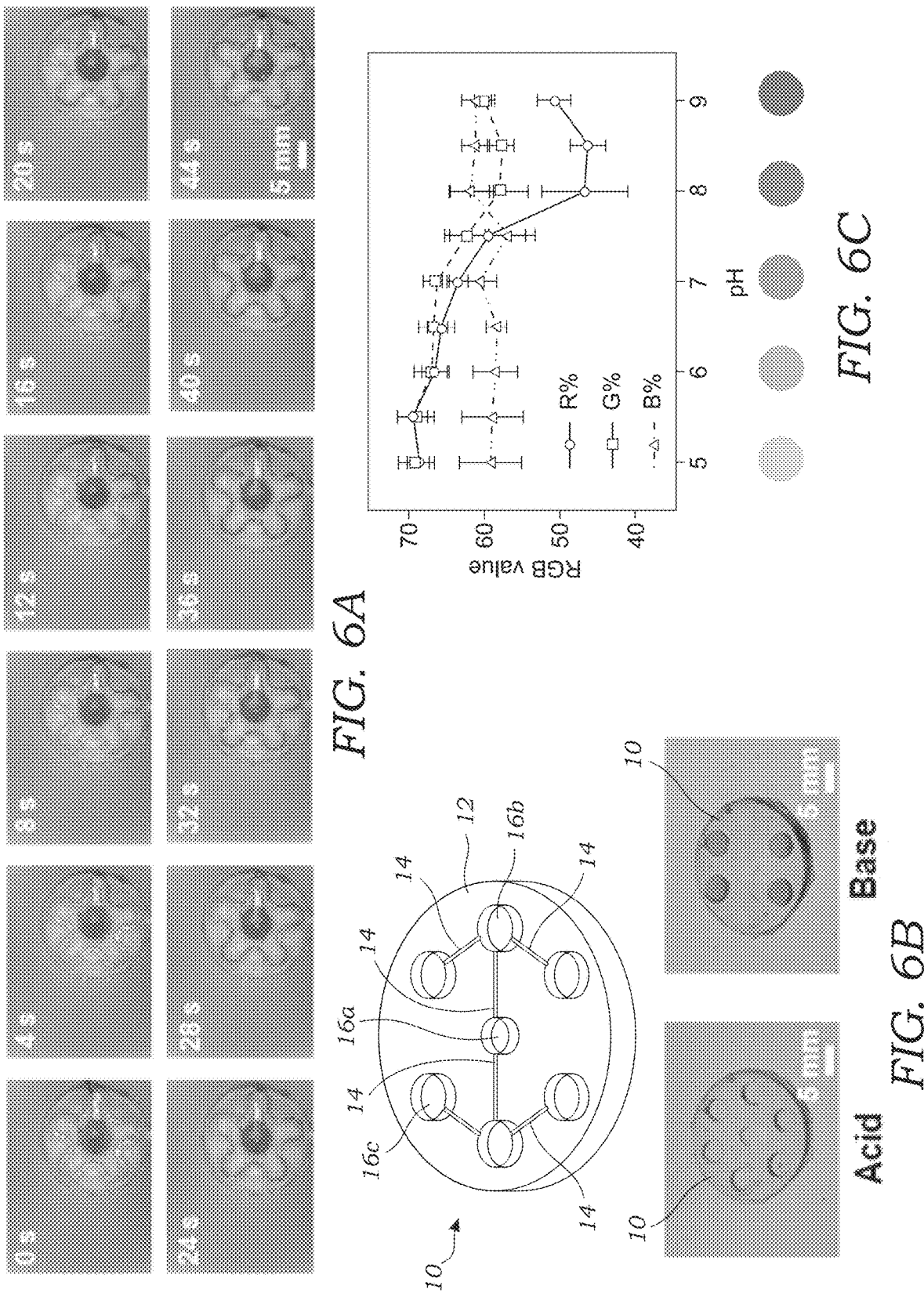
FIG. 6A illustrates a colorimetric contact lens biosensor located in microchannel-containing poly(HEMA) contact lens.
FIG. 6B schematically illustrates the poly(HEMA) microchannel based contact lens biosensor. The bottom shows the real color response of the pH colorimetric sensor to acid and base.
FIG. 6C illustrates the RGB triplet of the biosensor at different pH values ranging from 5.0 to 9.0 with a step of 0.5 in aqueous solutions (N=8). Inset shows the displayed color in the test chamber that filled with target solutions.

The ameliorated flows in hydrated poly(HEMA) hydrogel microchannels 14 encourages its application for wearable contact lens biosensing. Therefore, a fully wearable untethered colorimetric pH sensor 22 in these poly(HEMA) microchannels 14 (FIGS. 6A, 6B) was developed. The pH value of tears has therapeutic and diagnostic significance. The shift in pH values affects both cell viability and antibiotic effectiveness. Therefore, monitoring pH changes in tears can help in understanding the mechanisms of disease processes. As shown in FIG. 6A, spontaneous flow occurred in a poly (HEMA) contact lens 10 prototype where microchannels 14 were created (fully hydrated state, stage 3 in FIGS. 4B, 4H). The artificial tear of different pH values in the sampling chamber 16a (FIG. 6B) could spontaneously flow into the storing chambers 16b, and then to the sensing or testing chambers 16c through the microchannels 14 of the contact lens 10. The colorimetric pH indicator in the sensing or testing chamber 16c displayed different colors when interfacing with fluids of different pH values between 5 and 9 (FIG. 6C), which thoroughly covers the pH range of human tear (5-7.5). The detection time of the colorimetric indicator was about 5 min. The different colors may be determined through a manual inspection or by an image that is taken of the contact lens 10 (e.g., using a Smartphone or other reader/imaging device). The colors may preferably be ascertained while the contact lens 10 is being worn by the subject. The contact lens 10 may, in some embodiments, contain a number of sensing or testing chambers 16c to that multiple color signals may be read.

Figures 7A, 7B, 7C:
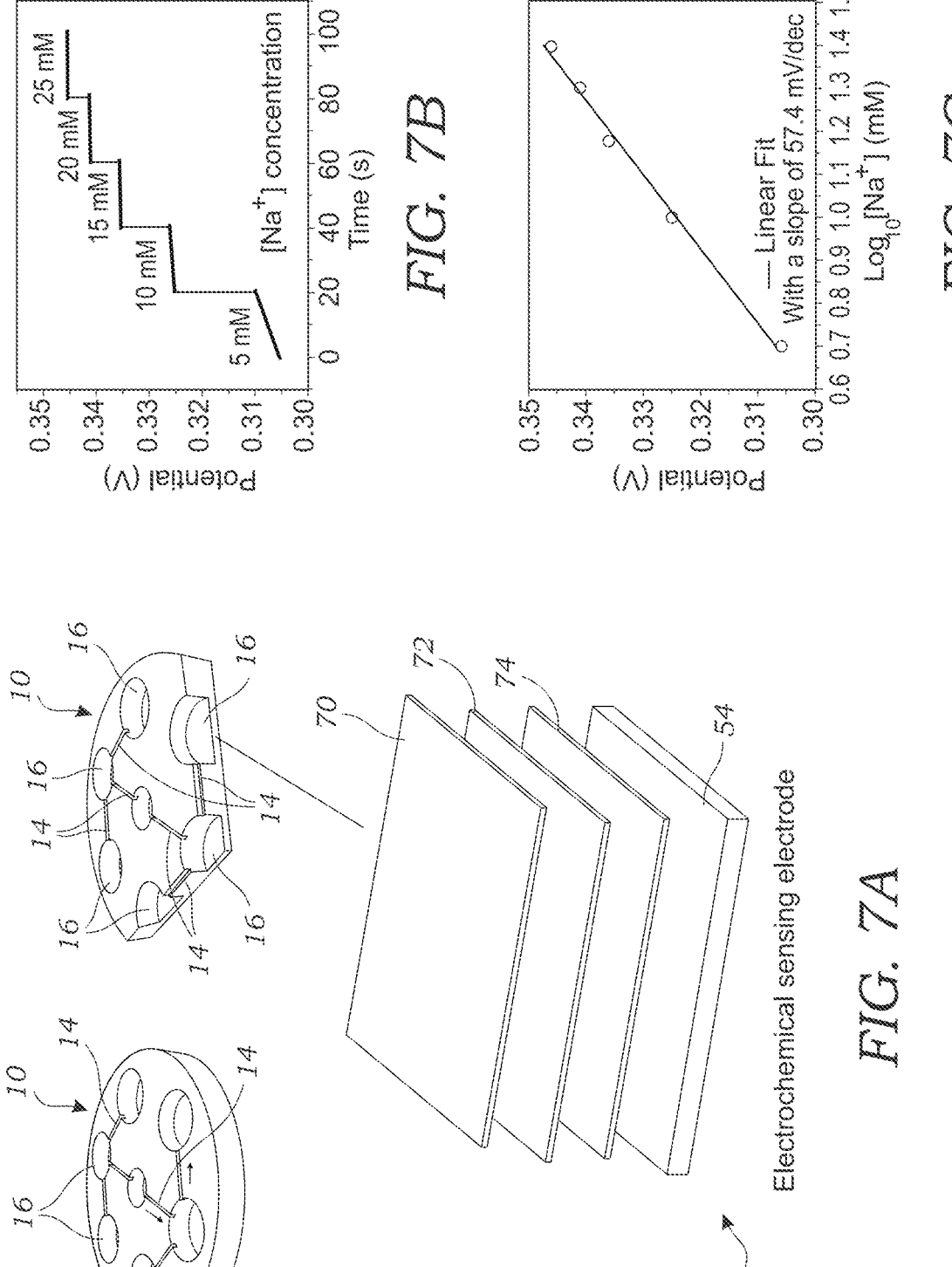
FIG. 7A schematically illustrates a potentiometric Na$^+$ sensing electrode located in poly(HEMA) hydrogel microchannels of a contact lens. The Na$^+$ electrochemical sensor was fabricated on PEDOT:PSS coated Parylene-C film and then bonded to poly(HEMA) chamber.
FIG. 7B is a graph of potential vs. time which shows the open-circuit potential increased with increased NaCl concentrations.
FIG. 7C illustrates a graph of potential vs. $\mathrm{Log}_{10}[\mathrm{Na}^+]$. A slope of 57.4 mV dec$^{-1}$ was obtained, which was close to the theoretical value of 59 mV dec$^{-1}$.

To further validate the promise of using poly(HEMA) hydrogel with microchannels 14 for contact lens biosensing, a Na⁺ electrochemical sensor 22 was integrated in the poly(HEMA) hydrogel's chambers 16. The concentration of Na is an essential health indicator in the tear that is relevant to tear osmolarity and dry-eye disease. In this embodiment, a flexible Na⁺ selective membrane 70 that contains a poly (3,4-ethylenedioxythiophene) polystyrene sulfonate (PEDOT:PSS) electrode 72 (deposited on Parylene substrate 74, FIG. 7A) could adhere firmly onto the poly(HEMA) hydrogel substrate 54 by using the hydrogel precursor as an adhesive promoter. FIG. 7B shows the potential response of the Na⁺ electrochemical sensor 22, potentiometrically measured in 5-25 mM NaCl solutions. The potential versus the Na⁺ concentration followed a linear relationship (FIG. 7C) with a slope of 57.4 mV dec⁻¹, which is in a good agreement with the theoretically predicted value of 59.2 mV dec⁻¹ (according to the Nernst equation at 25° C.). The detection range of the Na⁺ electrochemical sensor 22 is relevant to tear osmolarity monitoring and dry-eye disease diagnosis. As explained herein, a power source 24 and control circuitry 26 may be integrated into the contact lens 10 as illustrated in FIG. 1B. It is envisioned that further integration of an untethered colorimetric Na⁺ biosensor 22 in a poly(HEMA) contact lens 10 will promote its use for medical wearable applications.

Contact lenses 10 made from microchannel-containing poly(HEMA) hydrogels have been demonstrated with high-resolution 3D printing and replica molding. These microchannels 14 were encapsulated with either a plasma- or precursor-assisted bonding method. The flow dynamics in the poly(HEMA) microchannels 14 were qualitatively examined, and three flow regimes were found. Spontaneous Laplace pressure-driven capillary flow was observed in a fully hydrated sample. A peristaltic pressure-induced flow was observed in a mildly dehydrated sample. No flow was observed in a fully dehydrated sample. The observation of peristaltic pressure-driven flow is of importance because it indicates that eye-blinking pressure may help to promote tear flow in the microchannels 14 of the contact lens 10. A colorimetric pH sensor 22 and an electrochemical Na⁺ biosensor 22 were integrated onto a poly(HEMA) hydrogel contact lens 10.

Materials and Methods

Materials

HEMA, EGDMA, and BP were purchased from Sigma-Aldrich. Deionized (DI) water was obtained by Aqua Solutions Lab Water Systems. PDMS (SYLGARD 184) was purchased from the Dow Chemical Company. The resins used for 3D printing, B9R-1-Cherry, were obtained from B9Creations, LLC, and were used as received. Parylene C powder was purchased from Specialty Coating Systems Inc (SCS). PEDOT:PSS (Clevios™ PH1000) was purchased Haraeus Electronic Materials, Germany. 4-Dodecylbenzenesulfonic acid (DBSA), glycerol (99.5+ % purity), and (3-Glycidyloxypropyl)trimethoxysilane (GOPS) were purchased from Sigma-Aldrich. Sodium ionophore X (71747), bis(2-ethylhexyl) sebacate (DOS, 84822), sodium tetrakis [3,5-bis(trifluoromethyl)phenyl]borate (Na-TFPB, 692360), high-molecular-weight polyvinyl chloride (PVC) and tetrahydrofuran were purchased from Sigma-Aldrich. For flow visualization experiments, rhodamine B and tartrazine fluorescent dyes (Sigma-Aldrich) in deionized water were used. The bromothymol blue, methyl red, and phenolphthalein of the colorimetric pH sensing solution were purchased from Sigma-Aldrich and used without further purification.

Synthesis of Poly(HEMA) Hydrogel

Poly(HEMA) hydrogels were synthesized by free-radical polymerization of HEMA with 0.5 w/w % BP, as the free-radical initiator, and 1 v/v % EGDMA, as the cross-linking agent. For example, 40.3 mg BP, 6 mL HEMA, and 61 μL EGDMA were added to a mixing tube. This hydrogel precursor mixture was vortexed and sonicated until there were no visible solids. The mixture was then filled into a mold and de-gassed to prevent cavity or bubble formation in the final poly(HEMA) hydrogel. The fully crosslinked hydrogel was obtained after thermal curing the precursor in an oven at 80° C. for 1 hour.

Characterization of Poly(HEMA) Hydrogel

The contact angle of poly(HEMA) was tested by a goniometer (AST VCA-3000S Wafer Surface Analysis System, USA). The modulus of the poly(HEMA) hydrogels 54 was measured with an INSTRON tensile tester (INSTRON 5943, USA) in compression mode. The swelling ratio was tested by measuring the weight of the poly(HEMA) before and after immersion in DI water for varying time scales (0-60 hours). The original length, width, and height of poly (HEMA) hydrogel were 10 mm, 10 mm, 3 mm, respectively. N=3 for all the experiments.

Fabrication of Poly(HEMA) Hydrogel Microchannels

For the 3D-shaped poly(HEMA) microchannel fabrication, high-resolution molds 50 (FIG. 3A) were directly printed by a 3D printer (MONO3 DLP 3D Printer) with a resolution of 30 μm. The mold 50 was designed by computer-aided design (CAD) software. In this study, the width of the microchannels 14 was 100 or 200 μm, the depth was 100 or 200 μm, and the axial length was 16 mm. To ease the poly(HEMA) hydrogel 54 delamination, a 2 μm thick Parylene-C layer 52 was deposited on the 3D printed mold 50 using SCS Parylene Deposition System. Next, the poly (HEMA) precursor was cast onto the mold 50 and polymerized as described above. After polymerization, the poly (HEMA) hydrogel 54 adhered firmly to the 3D printed mold 50. The hydrogel 54 and mold 50 were immersed in water (80° C.) overnight to ease delamination. After removing the fully hydrated poly(HEMA) hydrogel 54 (or contact lens 10) from the oven, the hydrogel 54 or contact lens 10, with well-defined microchannels 14, was gently delaminated from the mold 50. The thickness of the poly(HEMA) hydrogel 54 ranged from 1 to 5 mm, depending on the volume of the HEMA precursor used. The final thickness of the crosslinked hydrogel was close to the height of the HEMA precursor solution that was placed in the hollow PDMS mold. That is, the hydrogel did not show significant shrinkage in the thickness direction after thermal crosslinking.

Encapsulation of Poly(HEMA) Hydrogel Microchannels

The thin poly(HEMA) hydrogel capping layer 20 was fabricated by injecting the precursor into a PDMS mold, followed by a thermal crosslinking process. To create the PDMS mold, poly(methyl methacrylate) (PMMA) was laser ablated to the desired shape (VLS 2.30, Universal Laser, USA). PDMS (10:1, SYLGARD 184) was poured onto a Petri dish containing the PMMA mold. The sample was then cured in an oven at 80° C. for 1 hour. Planar and concave PDMS sheets were then bonded together treated with oxygen plasma (2 min, oxygen flow rate of 35 cc/min, and power of ~120 W (PE-25, Plasma Etch Inc., USA)). Next, the poly(HEMA) precursor was injected into the PDMS mold, followed by a manually de-gassing process via syringe extraction. The sample was then placed in an 80° C. oven for 1 hour. After polymerization, the PDMS mold was manually separated, and the sample was immersed in water overnight in an 80° C. oven to enable the delamination of the poly(HEMA) hydrogel capping layer 20 from the PDMS.

To encapsulate these microchannels 14, the following two methods were used. In the first method, surfaces of the hydrated microchannel-containing hydrogel and capping layer 20 were both dried using a nitrogen gun, followed by oxygen plasma treatment for 2 min (10 cc/min, 160 W). Immediately after plasma treatment, the microchannel-containing hydrogel and capping layer 20 were first pressed together for 1 min and then placed in an 80° C. oven (1 hour) to further enhance the adhesion. In the second bonding method, the surface of the capping layer 20 was dried with a nitrogen gun before loading onto a spin-coater (WS-650-23B Spin-Coater). Approximately 20 μL of the poly(HEMA) precursor was spin-coated on the poly(HEMA) hydrogel capping layer 20 (500 rpm for 10 s, followed by 2000 rpm for 30 s). The microchannel-containing poly(HEMA) hydrogel 54 (or base layer 18 of contact lens 10) was then dried by nitrogen gas and pressed onto the precursor-coated poly (HEMA) capping layer 20, followed by a heating process (80° C. oven for 1 hour) for crosslinking.

Flow Visualization

Flow visualization in the microchannels 24 was recorded via a smartphone camera 68 (iPhone XR) integrated with a 10× macro lens of the flow visualization system 60. The smartphone was mounted on a z-stage 62 to ease position adjustment. The portable visualization setup allowed an easy adjustment of the camera lens to the desired direction. The peristaltic pressure application was enabled by the use of a speed controller (Oriental Motor BMUD30, USA), a motor or rotary actuator 64 (Oriental Motor BLM230HP, USA), a laser-ablated convex head 66, a z-stage 62, and a balance (as illustrated in FIG. 8A). The motor speed is adjustable between 1 and 100 rpm. The PMMA convex heads 66 were designed to have the shape of barrels (2 cm in diameter and 3 mm in length) with bumps of different angles obtained by laser ablation (VLS 2.30, Universal Laser, USA). Adjustment of the z-stage height controlled the applied force of convex heads 66 to the poly(HEMA) hydrogel capping layer 20. The pressure applied to the capping layer 20 was estimated by the following equation:

$$P = \frac{mg}{A}$$

Where m is the peak weight recorded by the underlying balance, g is the gravitational acceleration, and A is the contact area between the convex PMMA head 66 and the capping layer 20.

Fabrication of Colorimetric Sensor and Electrochemical Sensor Onto Poly(HEMA) Hydrogels The colorimetric pH indicator was prepared by mixing bromothymol blue (139 μg), methyl red (12 μg), and phenolphthalein (86 μg) in 100 μL of deionized water. The solution was loaded directly into the poly(HEMA) testing chambers 16c, after gentle resuspension. The sample was then placed in a desiccator for degassing (4 hours) to immobilize the pH colorimetric indicator onto poly(HEMA) testing chambers 16c. Then the sample was immersed in water (>2 hours) to fully hydrate poly(HEMA) hydrogel. For pH indication, the analyte (pH from 5.0 to 9.0, step 0.5) was loaded into the testing chambers 16c. The color of the indicator was recorded about 5 min after reacting with the analyte.

The $Na^+$ selective electrochemical sensing electrode 70 was obtained through the mixing of Na ionophore X (1%, w/w), DOS (65.45% w/w), PVC (33% w/w), and Na-TFPB (0.55% w/w). Next, 100 mg of the mixture was thoroughly dissolved in 660 μL of tetrahydrofuran. The ion-selective sensing electrode 22 was prepared by drop-casting 20 μL of the mixture 70 onto PEDOT:PSS film 72 (100 nm)/Parylene C (2 μm) 74. The modified electrode was dried in air for 6 hours. Parylene C film 74 was obtained through chemical vapor deposition with SCS coating systems. PEDOT:PSS (0.5 v/v. % DBSA, 5 v/v. % glycerol, and 1 v/v. % GOPS) was span-coated on Parylene C film 74 at 2000 rpm (30 s). The Na$^+$ selective electrode 70/72 on Parylene C film 74 was attached to the poly(HEMA) by using poly(HEMA) precursors as adhesion promoters. Full crosslinking of the precursors increased the Parylene C film 74 adhesion to the poly(HEMA) hydrogel. The measurement was performed with an electrochemical workstation (CH Instruments), where Ag/AgCl was used as the reference electrode and Pt wire was used as a counter electrode. Chronopotentiometry method was used for data collection without applying a current between the working electrode and the counter electrode While embodiments of the present invention have been shown and described, various modifications may be made without departing from the scope of the present invention. The invention, therefore, should not be limited, except to the following claims, and their equivalents.

What is claimed is:

1. A contact lens comprising:
a lens body comprising a base layer and a capping layer, both the base layer and the capping layer comprising poly-2-hydroxyethyl methacrylate (poly (HEMA)) hydrogel, the base layer having formed therein one or more microchannels and a plurality of chambers, the one or more microchannels connected to the plurality of chambers, the capping layer bonded to the base layer and overlying the one or more microchannels and the plurality of chambers;
an inlet fluidically coupled to one of the plurality of chambers and an outlet fluidically coupled to one of the plurality of chambers; and
an electrochemical sensing electrode disposed in one or more of the plurality of chambers or the one or more microchannels, wherein the electrochemical sensing electrode comprises poly (3,4-ethylenedioxythiophene) polystyrene sulfonate PEDOT:PSS) having a sodium ionophore disposed thereon.

2. The contact lens of claim 1, wherein one or more of the plurality of chambers are connected at least two microchannels.

3. The contact lens of claim 1, further comprising a therapeutic agent disposed in one or more of the plurality of chambers or the one or more microchannels.

4. The contact lens of claim 1, wherein the one or more microchannels have a width between about 10 μm and 800 μm.

5. The contact lens of claim 1, wherein the one or more microchannels have a height between about 10 μm and 800 μm.

6. The contact lens of claim 2, wherein one or more of the plurality of chambers comprises a reagent contained therein.

7. A method of forming a contact lens with one or more microchannels formed therein comprising:
(a) providing a mold having reverse features of the one or more microchannels and the plurality of chambers;
(b) casting poly-2-hydroxyethyl methacrylate (poly (HEMA)) precursor mixture on the mold, the precursor mixture comprising HEMA, a free-radical initiator, and a crosslinking agent to form a poly (HEMA) base layer;
(c) removing the poly (HEMA) base layer from the mold;
(d) subjecting the poly (HEMA) base layer to plasma treatment or applying the poly (HEMA) precursor mixture to the poly (HEMA) base layer after removing the poly (HEMA) base layer from the mold; and
(e) securing a poly (HEMA) capping layer to the poly (HEMA) layer after operation (d).

8. The method of claim 7, wherein the mold having the reverse features has a polymer anti-adhesion layer formed thereon.

9. The method of claim 7, further comprising flattening the poly (HEMA) base layer removed from the mold prior to securing the poly (HEMA) capping layer.

10. A method of using the contact lens of claim 1, comprising:
inserting the contact lens onto the eye of a mammalian subject.

11. The method of claim 10, wherein blinking of the eye causes fluid flow through the one or more microchannels.

12. The method of claim 11, wherein the flow comprises peristaltic pressure-induced flow.

13. The method of claim 11, wherein the flow comprises spontaneous capillary flow.

14. The method of claim 10, further comprising sensing the osmolarity of tear passing along one or more microchannels or one of the plurality of chambers with the electrochemical sensing electrode.

15. The method of claim 10, further comprising delivering a therapeutic agent contained in the contact lens to the eye of the mammalian subject.

16. The method of claim 15, wherein the therapeutic agent is disposed in the one or more microchannels or at least one of the plurality of chambers in dry form and solubilized by tear.

* * * * *